United States Patent [19]

Sagou et al.

[11] Patent Number: 4,788,347

[45] Date of Patent: Nov. 29, 1988

[54] PROCESS FOR PRODUCING FORMALDEHYDE

[75] Inventors: Masakazu Sagou, Tokyo; Hideyo Fujii, Ehime, both of Japan

[73] Assignee: Sumitomo Chemical Company, Ltd., Osaka, Japan

[21] Appl. No.: 98,274

[22] Filed: Sep. 18, 1987

[30] Foreign Application Priority Data

Sep. 24, 1986 [JP] Japan .................. 61-225530

[51] Int. Cl.$^4$ .................. C07C 47/04
[52] U.S. Cl. .................. 568/487
[58] Field of Search .................. 568/487, 493

[56] References Cited

U.S. PATENT DOCUMENTS

| | | | |
|---|---|---|---|
| 4,054,609 | 10/1977 | Osugi et al. | 568/487 |
| 4,544,773 | 10/1985 | Sagou | 568/487 |

FOREIGN PATENT DOCUMENTS

| | | | |
|---|---|---|---|
| 41-11853 | 6/1966 | Japan | 568/487 |
| 47-19251 | 11/1972 | Japan | 568/487 |
| 48-97808 | 3/1973 | Japan . | |
| 51-76209 | 7/1976 | Japan | 568/487 |
| 51-1407 | 8/1976 | Japan . | |
| 5412444 | 5/1977 | Japan . | |
| 2010037 | 1/1987 | Japan | 568/487 |

OTHER PUBLICATIONS

77 Chem. Abst. 87870$_y$ (1972), Saito et al.
80 Chem. Abst. 70325$_k$ (1974), Watanabe et al.
84 Chem. Abst. 84:104992 (1976), Osugi et al.
86 Chem. Abst. 86:170879$^m$ (1977), Osugi et al.
88 Chem. Abst. 88:61979$_q$ (1978), Osugi et al.
Abstract of U.S. Pat. No. 4,054,609 from Official Gazzette.

*Primary Examiner*—Werren B. Lone
*Attorney, Agent, or Firm*—Cushman, Darby & Cushman

[57] ABSTRACT

Formaldehyde is prepared by dehydrogenating methanol in the substantial absence of oxygen and in the presence of a catalyst which is a zinc-silicon complex oxide obtained by mixing a solution containing a zinc salt of an inorganic or organic acid with a solution containing an inorganic silicate compound, or by adding urea to a solution containing a zinc salt of an inorganic or organic acid and an organic silicate compound, until a precipitate is formed, and subsequently baking the precipitate at at least 500° C.

18 Claims, No Drawings

PROCESS FOR PRODUCING FORMALDEHYDE

The present invention relates to a process for producing formaldehyde. More particularly, it is concerned with an improved process for producing formaldehyde by dehydrogenation of methanol in the substantial absence of oxygen, in which the catalyst is a specific zinc-silicon complex oxide.

Formaldehyde is an important basic raw material in the chemical industry. It is used for the production of synthetic resins such as polyacetal resin, urea resin, and phenol-formaldehyde resin; and chemicals such as pentaerythritol and hexamethylenetetramine.

Formaldehyde is commercially produced from methanol by the silver-catalyzed oxidation-dehydrogenation in an air flow, or by a catalytic oxidation process which employs a mixture of iron oxide and molybdenum oxide as a catalyst in place of silver.

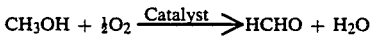

$$CH_3OH + \tfrac{1}{2}O_2 \xrightarrow{Catalyst} HCHO + H_2O$$

These processes, however, have some disadvantages. First, they need a complex and expensive equipment to protect the catalyst from deactivation and to remove by-products, and they also consume a large amount of steam and power. Secondly, they produce a large amount of water as a by-product and they produce formaldehyde in the form of 30–50% aqueous solution becausethe resultant formaldehyde is recovered by absorption into water. A large amount of water in the aqueous solution has to be removed in an instance where formaldehyde is used for the production of polyacetal resin, and this leads to a high energy cost.

In order to eliminate the disadvantages of the catalytic oxidation-dehydrogenation process and catalytic oxidation process, there have been proposed several catalytic dehydrogenation processes, by which formaldehyde is produced by dehydrogenating methanol in the substantial absence of oxygen.

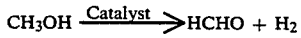

$$CH_3OH \xrightarrow{Catalyst} HCHO + H_2$$

The catalyst varies from one process to another. For example, in the process disclosed in Japanese Patent Publication No. 11853/1966, the catalyst is composed of copper, silver, and silicon; in the process disclosed in Japanese Patent Publication No. 19251/1972 and Japanese Patent Laid-open No. 97808/1983, the catalyst is molten zinc, gallium, indium, or aluminum; and in the process disclosed in Japanese Patent Laid-open Nos. 1407/1976, 76209/1976, and 215/1977, the catalyst is composed of copper, zinc, and sulfur or selenium. However, none of these catalysts are satisfactory in all of the basic performances required for catalysts such as yield, selectivity and life.

In order to address the above-mentioned problems involved in the catalytic dehydrogenation of methanol, the present inventors carried out a series of researches which matured into their previous inventions relating to a process which employs as a catalyst a metal oxide obtained by burning a specific zinc salt and/or indium salt, and a process which employs as a catalyst zinc oxide and/or indium oxide carried on silica. They are disclosed in Japanese Patent Laid-open No. 4147/1985 and Japanese Patent Publication No. 6629/1985.

As the result of their continued studies in search of an improved process for the production of formaldehyde, the present inventors have found that a catalyst composed of zinc-silicon complex oxide of specific composition permits the stable production of formaldehyde with high yield over a long period of time. The pesent invention is based on this finding.

It is an object of the present invention to provide an economically advantageous process for producing formaldehyde by dehydrogenating methanol in the substantial absence of oxygen, said process being characterized in that the dehydrogenation is performed by the aid of a catalyst which i a zinc-silicon complex oxide obtained by mixing a solution containing a zinc salt of an inorganic or organic acid with a solution containing an inorganic silicate compound, or by adding urea to a solution containing a zinc salt of an inorganic or organic acid and an organic silicate compound, thereby forming a precipitate, and subsequently baking the precipitate at 500° C. or higher.

According to the present invention, the catalyst used in the process is a zinc-silicon complex oxide of specific composition. An amount of zinc in the catalyst should be 5–75 wt %, preferably 20–60 wt %, and an amount of silicon in the catalyst should be in the range defined by the silicon-to-zinc atomic ratio of 1/10 to 10/1.

The zinc moiety of the catalyst may be obtained from a variety of zinc salts. They include zinc salts of inorganic aids such as nitrate and sulfate and zinc salts of organic acids such as carboxylates. Preferable among them are zinc nitrate and zinc carboxylate.

The silicon moiety of the catalyst may be obtained from a variety of inorganic silicates such as sodium silicate, potassium silicate, and ammonium silicate, and organic silicates exemplified below. Ammonium silicate is most desirable among inorganic silicates because it does not contain any alkali that might remain in the catalyst.

The organic silicates are ortho-silicates represented by the formula (I).

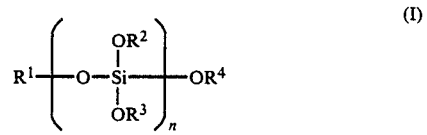

where $R^1$, $R^2$, $R^3$, and $R^4$ independently represent alkyl, alkenyl, alkynyl, aryl, aralkyl or organic carbonyl; and n is an integer from 1 to 10.

Examples of $R^1$, $R^2$, $R^3$, and $R^4$ include alkyl such as methyl, ethyl, n-propyl, i-propyl, n-butyl, i-butyl, sec-butyl, pentyl, cyclopentyl, hexyl, and cyclohexyl; alkenyl such as vinyl, propenyl, allyl, isopropenyl, and cyclohexenyl; alkynyl such as ethynyl and 2-propynyl; aryl such as phenyl, tolyl, and xylyl; aralkyl such as benzyl; and organic carbonyl such as formyl, acetyl, and propionyl.

Examples of the organic silicates include tetraalkyl silicates such as tetramethoxysilane and tetraethoxysilane and condensates thereof.

In the preparation of the catalyst, aqueous solution of the above-mentioned zinc salt and aqueous solution of the above-mentioned inorganic silicate are mixed together to form a precipitate. The mixing may be accomplished by adding the former to the latter, by adding the latter to the former, or by adding the both to each other simultaneously. The precipitation may be accomplished by controlling the pH with an acid (e.g., sulfuric acid and acetic acid) or an alkali (e.g., ammonia and sodium carbonate). The precipitation may be accomplished at any temperature, usually at room temperature.

In the case where aqueous solution of zinc salt and aqueous solution of organic silicate are used, precipitation is accomplished by the aid of urea as a precipitant. Any commercial urea suffices. The urea is used in an amount of 1–20 mol, preferably 2–10 mol, for 1 mol of zinc Only for the purpose of precipitation, the urea may be replaced by an alkali such as sodium hydroxide, potassium hydroxide, potassium hydrogen carbonate, sodium carbonate, sodium hydrogen carbonate, and ammonia, which is commonly used as a precipitant for metal ions. However, such an alkali precipitant provides a catalyst having a very small activity. However, the urea precipitant provides a catalyst which has not only an extremely large activity but also a longer life compared with any known catalysts.

The function of the urea is not fully elucidated yet. The fact that urea provides a catalyst having an extremely large specific surface area (measured by the BET method) suggests that urea causes the formation of zinc hydroxide and the hydrolysis of organic silicate to proceed simultaneously, thereby forming a precipitate of uniform composition.

The preparation of the catalyst from an organic silicate is carried out in the following manner. At first, a precursor of the zinc oxide and an organic silicate are dissolved in alcohol or water or a mixture thereof. The resulting solution is dissolved urea. Subsequently, the solution is heated at 60°–150° C. for 1–100 hours to bring about precipitation.

The precipitate formed in the above-mentioned manner is filtered off, washed, and dried. It is finally baked in an air stream or an inert gas stream at 500°–1200° C., preferably 600°–1100° C., and more preferably about 900°–1000° C. Thus there is obtained a catalyst which is characterized by that very little zinc is lost by reduction during reaction. The baking at about 900°–1000° C. affords a catalyst which maintains the activity for an extremely long period of time, with almost no loss of zinc. Presumably, this is because the baking at that temperature forms crystalline zinc ilicate ($Zn_2SiO_4$).

The catalyst obtained as mentioned above is used for the dehydrogenation of methanol which is usually performed in a flowing gas reaction system. In this reaction system, methanol is supplied in a gaseous form to the catalyst layer, which is usually kept at 450°–650° C., preferably 450°–550° C. The reaction may be carried out under any pressure, usually atmospheric pressure to 10 kg/cm$^2$.

Feed methanol may be diluted with an inert gas (e.g., nitrogen, methane, carbon dioxide) and/or hydrogen. Methanol should be fed at a rate of 0.1–10 kg/hr per kg of catalyst, depending on the volume and shape of the reactor. With a feed rate of less than 0.1 kg/hr, the reaction is not practical, and with a feed rate of more than 10 kg/hr, the conversion of methanol is small.

The product gas discharged from the reactor is cooled and then introduced to a heat-exchanger type condenser or an absorbing tower for the recovery of formaldehyde. Incidentally, the product gas contains water in a very small amount, say 0.01 mol or less for 1 mol of formaldehyde. This makes the process advantageous for the production of water-free high-purity formaldehyde. In the case where the absorbent is a higher alcohol such as polyethylene glycol, diethylene glycol, and cyclohexanol, formaldehyde is recovered in the form of hemiformal solution of higher alcohol. Upon thermal decomposition, it readily provides high-purity formaldehyde.

According to the process of the invention, the catalyst permits the production of formaldehyde in a high yield at a high conversion of methanol. Moreover, blocking of a catalyst and loss of zinc by reduction are so greatly controlled that production of formaldehyde is ensured for a long period of time with high yield. In addition the process of the invention provides formaldehyde containing a very small amount of water which is able to remove easily. The formaldehyde is especially suitable for the production of polyacetal and oil-soluble phenolic resin, in which contamination of water should be avoided. The production of formaldehyde by the process of this invention also affords a large amount of hydrogen (offgas) which can be effectively utilized as a heat source or feedstock.

The present invention, owing to the above-mentioned advantages, is also able to apply to the production of aldehydes or ketones through the dehydrogenation of the corresponding alcohols other than methanol, such as ethanol, butanol, isopropanol, and cyclohexanol.

The following examples will be helpful to further understand the invention.

(I) Preparation of Catalysts

Catalyst-A

Solution-A (aqueous solution of ammonium silicate $(NH_4)_2SiO_3$) was prepared by passing an aqueous solution of sodium silicate (15.3 g of $Na_2SiO_3 \cdot 9H_2O$ in 100 ml of distilled water) at a flow rate of 500 ml/min through a column filled with 400 ml of ion-exchange resin (Duorite C-22) which had previously been ion-exchanged into $NH_4$-type.

Solution-B (aqueous solution of zinc nitrate) was prepared by dissolving 37.2 g of zinc nitrate $Zn(NO_3)_2 \cdot 6H_2O$ in 100 ml of distilled water.

The solution-A was added dropwise with thorough stirring over 30 minutes to the solution-B which was heated at 60° C. After the addition, stirring was continued for additional 30 minutes. The resulting white slurry was filtered and the separated solids were washed with water and dried at 150° C. for 12 hours. The solids were baked at 340° C. for 2 hours in the air and further baked at 600° C. for 5 hours in an electric furnace. Thus there was obtained Catalyst-A.

Catalyst-A contains 43.1 wt % of zinc and 21.2 wt % of silicon, and has a specific surface area of 222.6 m$^2$/g (measured by the BET method). In addition, Catalyst-A contains amorphous $SiO_2$ and $ZnO$ according to X-ray diffractometry.

Catalyst-B

A white slurry was prepared according to the same procedure as in the production of Catalyst-A. The slurry was filtered and the separated solids were washed with water and dried at 150° C. for 12 hours. Using an electric furnace, the solids were baked at 350° C. for 2 hours in the air and further baked at 1000° C. for 5 hours. Thus there was obtained Catalyst-B.

Catalyst-B contains 43.1 wt % of zinc and 21.2 wt % of silicon, and has a specific surface area of 40.8 m$^2$/g (measured by the BET method). In addition, Catalyst-B contains amorphous $Zn_2SiO_4$ alone according to X-ray diffractometry.

Catalyst-C

Solution-B (aqueous solution of zinc nitrate) was prepared by dissolving 37.2 g of zinc nitrate $Zn(NO_3)_2.6H_2O$ in 100 ml of distilled water.

Solution-C (aqueous solution of sodium metasilicate $Na_2SiO_3.6H_2O$) was prepared by dissolving 15.3 g of sodium metasilicate in 100 ml of distilled water.

The solution-C was added dropwise with thorough stirring over 30 minutes to the solution-B which was heated at 60° C. After the addition, stirring was continued for further 30 minutes. The resulting white slurry was filtered and the separated solids were washed with water and dried at 150° C. for 12 hours. Using an electric furnace, the solids were baked at 350° C. for 2 hours in the air and further baked at 600° C. for 5 hours. Thus there was obtained Catalyst-C.

Catalyst-C contains 42.6 wt % of zinc and 21.5 wt % of silicon, and has a specific surface area of 138.0 m²/g (measured by the BET method). In addition, Catalyst-C contains amorphous $SiO_2$ and ZnO according to X-ray diffractometry.

Catalyst-D

In a mortar, 10 g of commercial zinc oxide ZnO and 7.48 g of silicon dioxide were thoroughly mixed. Using an electric furnace, the mixture was baked at 350° C. for 2 hours in the air and further baked at 1000° C. for 5 hours. Thus there was obtained Catalyst-D.

Catalyst-D contains 46.0 wt % of zinc and 20.0 wt % of silicon, and has a specific surface area of 91.1 m²/g (measured by the BET method).

Catalyst-E

In a mortar, 20 g of commercial zinc oxide ZnO and 7.48 g of silicon dioxide were thoroughly mixed. Using an electric furnace, the mixture was baked at 350° C. for 2 hours in the air and further baked at 1000° C. for 5 hours. Thus there was obtained Catalyst-E.

Catalyst-E contains 58.8 wt % of zinc and 12.7 wt % of silicon, and has a specific surface area of 62.5 m²/g (measured by the BET method).

Catalyst-F

A half of Catalyst-D was baked at 1300° C. for 3 hours in the air to give Catalyst-F.

Catalyst-F contains 46.0 wt % of zinc and 20.0 wt % of silicon, and has a specific surface area of 0.6 m²/g (measured by the BET method).

Catalyst-G

A half of Catalyst-E was further baked at 1300° C. for 3 hours in the air to give Catalyst-G.

Catalyst-G contains 58.8 wt % of zinc and 12.7 wt % of silicon, and has a specific surface area of 0.3 m²/g (measured by the BET method).

Catalyst-H

Solution-C (aqueous solution of zinc nitrate) was prepared by dissolving 14.6 g of zinc nitrate $Zn(NO_3)_2.6H_2O$ in 200 ml of distilled water. To solution-C was added 20 g of silicon dioxide. The resulting slurry mixture was thoroughly mixed on a water bath at 80° C. for 1 hour, and subsequently dried under reduced pressure in a rotary evaporator. The resulting solids were baked at 350° C. for 2 hours in the air and further baked at 600° C. for 5 hours in an electric furnace. Thus there was obtained Catalyst-H.

Catalyst-H contains 12.9 wt % of zinc and 38.0 wt % of silicon, and has a specific surface area of 75.0 m²/g (measured by the BET method).

Catalyst-I

The same procedure as in the preparation of Catalyst-H was repeated to give Catalyst-I, except that the baking at 600° C. for 5 hours was changed to 1000° C. for 5 hours.

Catalyst-I contains 12.9 wt % of zinc and 38.0 wt % of silicon, and has a specific surface area of 125.0 m²/g (measured by the BET method).

Catalyst-J

Solution-C (aqueous solution of zinc nitrate) was prepared by dissolving 7.4 g of zinc nitrate in 200 ml of distilled water. To solution-C was added 25 g of silica sol (trade name "Snowtex N", containing 20 wt % of $SiO_2$). The resulting slurry mixture was thoroughly mixed on a water bath at 80° C. for 1 hour, and subsequently dried under reduced pressure in a rotary evaporator. The resulting solids were baked at 350° C. for 2 hours in the air and further baked at 600° C. for 5 hours in an electric furnace. Thus there was obtained Catalyst-J.

Catalyst-J contains 12.9 wt % of zinc and 38.0 wt % of silicon, and has a specific surface area of 135.6 m²/g (measured by the BET method).

Catalyst-K

A half of Catalyst-J was further baked at 1000° C. for 3 hours in the air to give Catalyst-K.

Catalyst-K contains 12.9 wt % of zinc and 38.0 wt % of silicon, and has a specific surface area of 65.89 m²/g (measured by the BET method).

Catalyst-L

In 100 g of ethanol was dissolved 23.93 g of zinc nitrate $Zn(NO_3)_2.6H_2O$. To the resulting solution added 16.66 g of tetraethoxysilane, followed by stirring for 30 minutes at room temperature. To the solution was added urea solution (28.8 g of urea in 84.6 g of distilled water), followed by stirring at room temperature for 30 minutes. The solution temperature was raised to 80° C. with stirring, and stirring was continued at that temperature for 9 hours to give a white slurry liquid. After being filtered and washed with water, the white solids were dried at 150° C. for 12 hours. The dried solids were baked at 350° C. for 2 hours in the air and further baked at 600° C. for 5 hours in an electric furnace. Thus there was otbained Catalyst-L.

Catalyst-L contains 36.2 wt % of zinc and 25.5 wt % of silicon, and has a specific surface area of 296.5 m²/g (measured by the BET method).

Catalyst-M

The same procedure as in the preparation of Catalyst-L was repeated to give Catalyst-M, except that the urea solution was replaced by 58.3 g of 28 wt % ammonia water which was added dropwise with stirring over 30 minutes.

Catalyst-M contains 34.6 wt % of zinc and 24.5 wt % of silicon, and has a specific surface area of 6.6 m²/g (measured by the BET method).

Catalyst-N

In 39.5 g of ethanol was dissolved 53.4 g of zinc nitrate $Zn(NO_3)_2.6H_2O$. To the resulting solution were added 37.2 g of tetraethoxysilane dissolved in 39.5 g of ethanol, followed by stirring for 30 minutes at room temperature. To the solution was added urea solution (61.5 g of urea in 150 g of distilled water), followed by stirring at room temperature for 30 minutes. The solution temperature was raised to 80° C. with stirring, and stirring was continued at that temperature for 6 hours to give a white slurry liquid. After being filtered and washed with water, the white solids were dried at 150° C. for 12 hours. The dried solids were baked at 350° C. for 2 hours in the air and further baked at 600° C. for 1 hour in an electric furnace. Thus there was obtained Catalyst-N.

Catalyst-N contains 44.6 wt % of zinc and 19.5 wt % of silicon, and has a specific surface area of 225 m$^2$/g (measured by the BET method).

Catalyst-O

The same procedure as in the preparation of Catalyst-N was repeated to give Catalyst-O, except that the amount of zinc nitrate was 26.7 g in place of 53.4 g, the amount of urea 30.7 g in place of 61.5 g, and the amount of distilled water (as a solvent of urea) 170 g in place of 150 g.

Catalyst-O contains 31.3 wt % of zinc and 27.7 wt % of silicon, and has a specific surface area of 371 m$^2$/g (measured by the BET method).

Catalyst-P

In 200 ml of water was dissolved 18.27 g of zinc nitrate Zn(NO$_3$)$_2$.6H$_2$O. To the resulting solution was added 25 g of silica sol (tradename "Snowtex N" produced by Nissan Kagaku Co., Ltd. containing 20 wt % of SiO$_2$) The resulting slurry mixture was thoroughly mixed on a water bath at 80° C. for 1 hour, and subsequently dried under reduced pressure in a rotary evaporator. The resulting solids were baked at 350° C. for 2 hours in the air and further baked at 600° C. for 5 hours in an electric furnace. Thus there was obtained Catalyst-P.

Catalyst-P contains 40.2 wt % of zinc and 23.4 wt % of silicon, and has a specific surface area of 78 m$^2$/g (measured by the BET method).

The above-mentioned catalysts A to P were granulated into 24-48 mesh particles. They were stored in a desiccator.

The specific surface area was measured with "Monosorb" (tradename made by Quantachrome) after dehydration in a nitrogen stream at 200° C. for 30 minutes.

(II) Catalyst reaction test

To evaluate the catalysts prepared as mentioned above, the dehydrogenation of methanol was carried out by passing a methanol-nitrogen mixture (CH$_3$OH/N$_2$=18/32 in mol), which had previously been vaporized at 150° C., through a tubular quartz reactor, 10 mm in inside diameter, filled with 1.0 g of the sample catalyst. The reaction temperature was 520°-550° C. and the flow rate was 550 mmol/hr under atmospheric pressure.

A gas from the reactor was subjected, by means of a heat-insulated gas sampler, to a gas chromatography (thermal conductivity detector) equipped with a 6-m column (APS-201, 20% Fulsin T, made by Gasukuro Kogyo Inc.) and a 2-m column (molecular sieve 13x), to effect quantitative analysis of formaldehyde [HCHO], methyl formate, dimethyl ether, hydrogen [H$_2$], carbon monoxide [CO], methane [CH$_4$], unaltered methanol [CH$_3$OH at the exit], and nitrogen. The results are shown in Tables 1 and 2. (The gas chromatography detected almost no methyl formate and dimethyl ether.)

Conversion rate of methanol, yield of formaldehyde, and selectively of formaldehyde are calculated according to the following equations.

$$\text{Conversion rate of methanol (\%)} = \left(1 - \frac{[CH_3OH]}{[HCHO] + [CO] + [CH_4] + 2[DME] + [CH_3OH]}\right) \times 100$$

$$\text{Yield of formaldehyde (\%)} = \frac{[HCHO]}{[HCHO] + [CO] + [CH_4] + 2[DME] + [CH_3OH]} \times 100$$

$$\text{Selectivity of formaldehyde (\%)} = \frac{[HCHO]}{[HCHO] + [CO] + [CH_4] + 2[DME]} \times 100$$

where [HCHO], [CO], [CH$_4$], and [DME] represent the rate (mmol/hr) at which the respective components are formed, and [CH$_3$OH] represents the flow rate (mmol/hr) of unaltered methanol measured at the exit of the reactor tube.

TABLE 1

Results of Reaction Test

| | Catalyst | Time (hr) | Conversion of CH$_3$OH (%) | Yield of HCHO (%) | Selectivity of HCHO (%) |
|---|---|---|---|---|---|
| Example | | | | | |
| 1* | A | 50 | 55.7 | 50.2 | 87.0 |
| | | 100 | 51.6 | 46.0 | 89.2 |
| | | 200 | 47.8 | 43.4 | 90.9 |
| | | 300 | 47.0 | 42.7 | 90.9 |
| | | 400 | 45.9 | 42.1 | 91.9 |
| 2 | A | 50 | 65.3 | 58.7 | 90.0 |
| | | 100 | 58.7 | 54.2 | 92.4 |
| | | 200 | 54.1 | 50.9 | 94.0 |
| | | 300 | 47.6 | 45.1 | 94.7 |
| | | 400 | 44.2 | 41.3 | 93.5 |
| 3 | B | 50 | 46.4 | 40.8 | 87.9 |
| | | 100 | 46.3 | 40.7 | 87.9 |
| | | 200 | 51.1 | 42.8 | 83.9 |
| | | 300 | 50.0 | 41.5 | 83.0 |
| | | 400 | 51.5 | 42.1 | 81.8 |
| | | 500 | 49.2 | 40.0 | 81.5 |
| 4 | C | 50 | 33.2 | 31.3 | 94.1 |
| | | 100 | 33.4 | 31.9 | 95.4 |
| Comparative Example | | | | | |
| 1 | D | 50 | 59.0 | 39.9 | 67.6 |
| | | 100 | 54.5 | 37.2 | 68.2 |
| 2 | E | 10 | 42.7 | 38.5 | 90.2 |
| | | 20 | 36.2 | 33.0 | 91.1 |
| 3 | F | 10 | 19.9 | 19.4 | 97.5 |
| | | 20 | 13.4 | 13.2 | 98.4 |
| 4 | G | 10 | 32.8 | 30.5 | 93.1 |
| | | 20 | 29.2 | 27.3 | 93.5 |
| 5 | H | 20 | 40.8 | 38.7 | 95.1 |
| | | 50 | 24.6 | 24.0 | 97.4 |
| 6 | I | 10 | 22.6 | 21.6 | 95.8 |
| | | 20 | 14.1 | 13.7 | 97.1 |
| 7 | J | 50 | 34.0 | 32.3 | 94.9 |
| | | 100 | 29.6 | 29.3 | 95.5 |
| 8 | K | 2 | 5.3 | 5.2 | 97.7 |
| | | 4 | 4.2 | 3.7 | 87.5 |

*Reaction temperature: 520° C. in Example 1 and 550° C. in other examples

TABLE 2

| | | Results after 20 hours of reaction | | | Results after 50 hours of reaction | | |
|---|---|---|---|---|---|---|---|
| | Catalyst | Conversion of CH$_3$OH (%) | Yield of HCHO (%) | Selectivity of HCHO (%) | Conversion of CH$_3$OH (%) | Yield of HCHO (%) | Selectivity of HCHO (%) |
| Example | | | | | | | |
| 5 | L | 63.7 | 59.3 | 93.2 | 60.3 | 57.1 | 94.7 |
| 6 | N | 75.2 | 58.6 | 78.0 | 68.2 | 64.0 | 93.9 |
| 7 | O | 58.1 | 53.0 | 91.2 | 41.4 | 39.4 | 95.1 |
| 8 | L | 52.4 | 48.5 | 92.6 | 48.6 | 45.5 | 93.7 |
| Comparative Example | | | | | | | |
| 9 | M | 26.4 | 26.0 | 98.5 | — | — | — |
| 10 | P | 33.0 | 32.0 | 96.9 | 26.4 | 25.7 | 97.5 |

Feed methanol was diluted with nitrogen in Examples 5 to 7 and Comparative Examples 9 and 10.
Feed methanol was diluted with hydrogen in Example 8.

What is claimed is:

1. A process for producing formaldehyde comprising: dehydrogenating methanol in the substantial absence of oxygen wherein the dehydrogenation is performed in the presence of a catalyst which is a zinc-silicon complex oxide obtained by
   (A) either (i) mixing a solution containing a zinc salt of an inorganic or organic acid with a solution containing an inorganic silicate compound, or (ii) adding urea to a solution containing a zinc salt of an inorganic or organic acid and an organic silicate compound until a precipitate is formed; and
   (B) subsequently baking the precipitate at a temperature of at least 500° C.

2. A process set forth in claim 1, wherein the baking temperature is 500°–1200° C.

3. A process set forth in claim 1, wherein the baking temperature is 600°–1100° C.

4. A process set forth in claim 1, wherein the zinc-silicon complex oxide contains 20–60% of zinc.

5. A process set forth in claim 1, wherein the zinc-silicon complex oxide contains crystalline zinc silicate (Zn$_2$SiO$_4$).

6. A process set forth in claim 1, wherein the zinc salt of inorganic acid is a nitrate.

7. A process set forth in claim 1, wherein the zinc salt of organic acid is an organic carboxylate.

8. A process set forth in claim 1, wherein the inorganic silicate compound is sodium silicate, potassium silicate, or ammonium silicate.

9. A process set forth in claim 1, wherein the organic silicate compound is tetraalkyl silicate.

10. A process set forth in claim 1, wherein the catalyst layer is kept at 450°–650° C. in the dehydrogenation.

11. A process set forth in claim 1, wherein the feed methanol is diluted with nitrogen, carbon dioxide, and/or hydrogen.

12. The process for producing high-purity formaldehyde consisting essentially of:
    dehydrogenating methanol in a flowing gas reaction system in the substantial absence of oxygen in the presence of a zinc-silicon complex oxide obtained by:
    (A) mixing a solution containing (a) a zinc carboxylate or a zinc salt of an inorganic acid with (b) a solution containing an inorganic silicate compound selected from the group consisting of sodium silicate, potassium silicate, and ammonium silicate; and
    (B) subsequently baking the thus obtained precipitate at a temperature of from least 500° C. to about 1200° C. wherein
    said catalyst contains 5–75 Wt. % zinc and an amount of silicon such that the atomic ratio of silicon/zinc is 1:10 to 10:1,
    the feed rate of methanol to said catalyst is about 0.1 to 10 kg/hr per kg of said catalyst, and
    the catalyst is in a layer at a temperature of about 450° C. to about 650° C.

13. The process according to claim 12, wherein said catalyst is baked at a temperature of from about 900° C. to about 1000° C.

14. The process according to claim 12, wherein the zinc salt is zinc nitrate and the inorganic silicate is ammonium silicate.

15. The process of producing high-purity formaldehyde consisting essentially of:
    dehydrogenating methanol in a flowing gas reaction system in the substantial absence of oxygen in the presence of a zinc-silicon complex oxide obtained by:
    (A) adding a selected amount of urea in the range of 1–20 mol per urea per mol of zinc of a solution obtained by mixing (a) a zinc carboxylate or a zinc salt of an inorganic acid with (b) a solution containing an organic silicate compound represented by the formula:

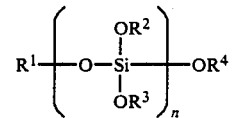

wherein said formula R$^1$, R$^2$, R$^3$, and R$^4$ independently represent alkyl, alkenyl, alkynyl, aryl, aralkyl or organic carbonyl and n is an integer from 1 to 10, whereby a precipitate is obtained; and
    (B) subsequently baking the thus obtained precipitate at a temperature of from least about 500° C. to about 1200° C. wherein
    said catalyst contains 5–75 wt. % zinc and an amount of silicon such that the atomic ratio of silicon/zinc is 1:10 to 10:1,
    the feed of methanol to said catalyst is at a rate of about 0.1 to 10 kg/hr per kg catalyst, and
    the catalyst is in a layer at a temperature of about 450° C. to about 650° C.

16. The process according to claim 15, wherein said catalyst is baked at a temperature of from 900° C. to 1000° C.

17. The process according to claim 15, wherein the zinc salt is zinc nitrate.

18. The process of according to claim 15, wherein the organic silicate is tetraalkyl silicate.

* * * * *